US006944549B2

(12) United States Patent
McClure

(10) Patent No.: US 6,944,549 B2
(45) Date of Patent: Sep. 13, 2005

(54) METHOD AND APPARATUS FOR AUTOMATED DETECTION OF PEAKS IN SPECTROSCOPIC DATA

(75) Inventor: Thomas D. McClure, La Jolla, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 10/280,232

(22) Filed: Oct. 25, 2002

(65) Prior Publication Data

US 2004/0083063 A1 Apr. 29, 2004

(51) Int. Cl.[7] ............................................. G01N 31/00
(52) U.S. Cl. ........................................ 702/22; 250/281
(58) Field of Search .............................. 702/22, 23, 27, 702/30–32, 66, 76, 189; 73/23.36; 250/282, 252.1, 187, 281; 435/6, 7.92

(56) References Cited

U.S. PATENT DOCUMENTS

| | | | | |
|---|---|---|---|---|
| 4,528,080 A | * | 7/1985 | Donohue et al. | 204/157.3 |
| 4,916,313 A | * | 4/1990 | Hall et al. | 250/282 |
| 5,121,337 A | * | 6/1992 | Brown | 702/28 |
| 5,526,682 A | | 6/1996 | Jarrell et al. | 73/61.55 |
| 5,538,897 A | | 7/1996 | Yates, III et al. | 436/89 |
| 5,885,841 A | * | 3/1999 | Higgs et al. | 436/89 |
| 5,993,662 A | | 11/1999 | Garr et al. | 210/656 |
| 6,008,490 A | * | 12/1999 | Kato | 250/282 |
| 6,017,693 A | | 1/2000 | Yates, III et al. | 435/5 |
| 6,147,344 A | | 11/2000 | Annis et al. | 250/281 |
| 6,339,950 B1 | * | 1/2002 | Bengsch et al. | 73/23.36 |
| 6,393,368 B1 | * | 5/2002 | Ito et al. | 702/22 |
| 6,418,383 B1 | * | 7/2002 | Wang | 702/22 |
| 6,430,512 B1 | * | 8/2002 | Gallagher | 702/22 |
| 6,487,523 B2 | * | 11/2002 | Jarman et al. | 702/189 |
| 6,581,013 B1 | * | 6/2003 | Annis et al. | 702/27 |
| 2002/0102572 A1 | * | 8/2002 | Crooke et al. | 435/6 |
| 2003/0087322 A9 | * | 5/2003 | Aebersold et al. | 435/7.92 |
| 2003/0109990 A1 | * | 6/2003 | Axelsson | 702/27 |

FOREIGN PATENT DOCUMENTS

| | | |
|---|---|---|
| EP | 0486030 A3 | 11/1991 |
| EP | 0486030 B1 | 11/1991 |
| EP | 0486030 A2 | 11/1991 |

OTHER PUBLICATIONS

What is AMDIS?, Kind, Tobias, 2002; www.amdis.net.

* cited by examiner

Primary Examiner—Marc S. Hoff
Assistant Examiner—Mohamed Charioui
(74) Attorney, Agent, or Firm—Jenkins, Wilson & Taylor P.A.

(57) ABSTRACT

A method and apparatus are provided for identifying peaks in spectral data. A method in accordance with some embodiments includes sorting the spectral data by spectral parameter values; detecting peaks in the data; integrating peak areas; identifying any coeluting peaks, and combining coeluting peak areas determined to be associated with the same compound; and generating a list of detected peaks and their corresponding areas, including any combined coeluting peak areas.

45 Claims, 4 Drawing Sheets

METHOD AND APPARATUS FOR AUTOMATED DETECTION OF PEAKS IN SPECTROSCOPIC DATA

BACKGROUND OF THE INVENTION

1. Field of the Invention

The present invention relates generally to analysis of spectral data and, in particular, to automated detection of peaks in such data.

2. Description of Related Art

Chromatographic separation devices are often used with detection devices such as spectrometers in investigating molecular structure of samples. These chromatographic separation devices allow compounds in a mixture being studied to be separated, and the amounts of the separated compounds detected. Representative chromatographic separation devices include, e.g., gas chromatography (GC) and high performance liquid chromatography (HPLC) devices.

Compounds separated by the chromatographic separation devices are typically introduced individually in time to detection devices such as spectrometers, which provide information on the identity of the compound being detected. Various types of spectroscopic approaches are commonly used including, e.g., mass spectrometry, ultraviolet spectroscopy, infrared spectroscopy, atomic spectroscopy, NMR spectroscopy, raman spectroscopy, emission spectroscopy, and the like.

The data generated from such compound analysis is three dimensional, providing information on time, intensity, and a spectral parameter (e.g., mass) related to the type of spectrometer used. The time information indicates at what time a compound separated by the chromatographic separation device arrived at the spectrometer. The intensity information indicates the intensity of each signal in the spectrum, which indicates the amount of the compound. The spectral parameter data provides information on the structure of the compound.

Various problems are encountered using these current methods of compound analyses. For example, the spectral parameter values of interest are very often masked by background signals. Also, in a complex mixture, multiple analytical signals can overlap and mask a less intense analyte. In addition, it is difficult and time consuming to analyze large sets of data as numerous analyses need to be performed quickly with high precision and accuracy.

A need accordingly exists for improved methods and apparatus for compound analysis.

SUMMARY OF VARIOUS ASPECTS OF THE INVENTION

In accordance with one aspect of the invention, a method is provided for identifying peaks in spectral data. The method includes: sorting the spectral data by spectral parameter values; detecting peaks in the data; integrating peak areas; identifying any coeluting peaks, and combining coeluting peak areas determined to be associated with the same compound; and generating a list of detected peaks and their corresponding areas, including any combined coeluting peak areas.

In accordance with one embodiment, the method further includes converting the spectral data to an instrument independent common format. In accordance with another embodiment, the method further includes smoothing the spectral data prior to integration. In accordance with yet another embodiment, the method further includes identifying and removing any isotopic peaks from the detected peaks.

In another aspect of the invention, a computer program product in computer-readable media is provided for identifying peaks in spectral data. The computer program product includes instructions enabling a computer to: sort the spectral data by spectral parameter values; detect peaks in the data; integrate peak areas; identify any coeluting peaks, and combine coeluting peak areas determined to be associated with the same compound; and generate a list of detected peaks and their corresponding areas, including any combined coeluting peak areas.

In accordance with one embodiment, the computer program product further includes instructions enabling a computer to convert the spectral data to an instrument independent common format. In accordance with another embodiment, the computer program product further includes instructions enabling a computer to smooth the spectral data prior to integration. In accordance with yet another embodiment, the computer program product further includes instructions enabling a computer to identify and remove any isotopic peaks from the detected peaks.

In accordance with another aspect of the invention, a system is provided for generating spectral data and for identifying peaks therein. The system includes a spectrometer for generating the spectral data from a sample and a computer system for analyzing the data. The computer system includes at least one processor, memory associated with the at least one processor, a display and a program supported in the memory for identifying peaks in spectral data. The program includes instructions enabling the computer system to: sort the spectral data by spectral parameter values; detect peaks in the data; integrate peak areas; identify any coeluting peaks, and combine coeluting peak areas determined to be associated with the same compound; and generate a list of detected peaks and their corresponding areas, including any combined coeluting peak areas.

In accordance with one embodiment, the program further includes instructions enabling a computer to convert the spectral data to an instrument independent common format. In accordance with another embodiment, the program further includes instructions enabling the computer system to smooth the spectral data prior to integration. In accordance with yet another embodiment, the program further includes instructions enabling the computer system to identify and remove any isotopic peaks from the detected peaks.

These and other features and aspects of the present invention will become readily apparent from the following detailed description wherein embodiments of the invention are shown and described by way of illustration of the best mode of the invention. As will be realized, the invention is capable of other and different embodiments and its several details may be capable of modifications in various respects, all without departing from the invention. Accordingly, the drawings and description are to be regarded as illustrative in nature and not in a restrictive or limiting sense.

BRIEF DESCRIPTION OF THE DRAWINGS

For a fuller understanding of the nature and objects of the present invention, reference should be made to the following non-limiting detailed description taken in connection with the accompanying drawings wherein.

DETAILED DESCRIPTION

The present invention is generally directed to methods and apparatus for automated peak detection in spectral data. The automated peak detection in accordance with various aspects and embodiments of the invention is especially suited for use in chromatography-spectrometry systems. It is particularly useful when compound related signals are reduced or obscured by interference and background signals. Integrated peak lists are generated in which the peaks are identified at individual spectral parameter values throughout the entire range of such values scanned by the spectrometer such that low abundance signals are not lost in the presence of high abundance signals. The integrated data is background subtracted and peak-overlap resolved.

Figure 1:
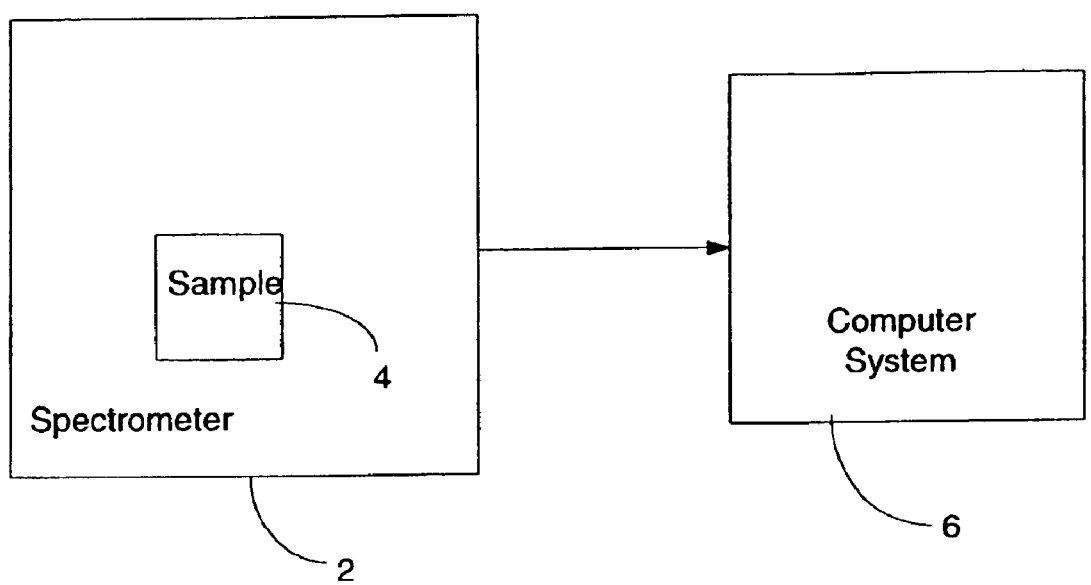
FIG. 1 is a schematic block diagram illustrating a system for collecting and analyzing chromatography-spectrometry data in accordance with some embodiments of the invention.

FIG. 1 illustrates a representative non limiting system for collecting and analyzing chromatography-spectrometry data in accordance with some embodiments of the invention. A spectrometer 2 analyzes a sample 4 introduced therein and generates chromatography-spectrometry data relating to the sample. This data is transmitted to a computer system 6, which executes a program for automated peak detection, which will be described in further detail below.

The spectrometer 2 can be, e.g., a mass spectrometer. As will be described below, various other spectroscopic approaches can also be used.

The computer system can comprise a general purpose computer. A representative computer is a personal computer or workstation platform that is, e.g., Intel Pentium, PowerPC or RISC based, and includes an operating system such as Windows, OS/2, Unix or the like. As is well known, such machines include a display interface (a graphical user interface or "GUI") and associated input devices (e.g., a keyboard or mouse).

Use of other computer systems is also possible. For example, the computer system can comprise multiple computers such as a client machine (e.g., a workstation) linked to a computer server. The client machine can receive data from the spectrometer 2 and transmit the data to the computer server, which processes the data. This arrangement is particularly useful when data from multiple spectrometers is transmitted to the server to be processed in parallel. The server computer is preferably a multiprocessor computer.

Figure 2:
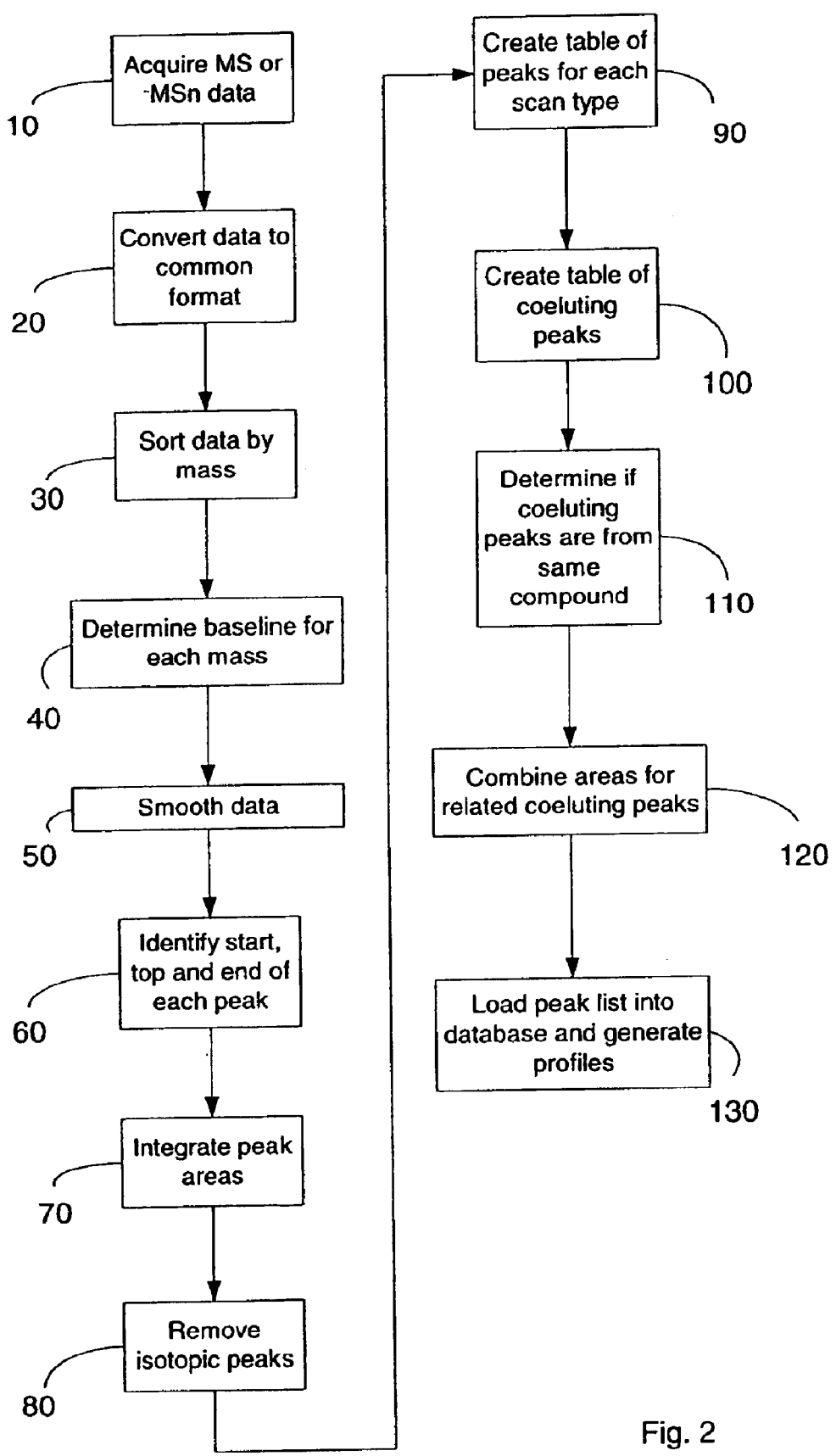
FIG. 2 is a flow chart generally illustrating the automated process for detecting peaks in the data in accordance with some embodiments of the invention.

FIG. 2 is a flow chart generally illustrating the process for peak detection in accordance with some embodiments of the invention. The process can be performed, e.g., by the computer system 6. For illustrative purposes, the process is described using a mass spectrometer. It should be understood that use of other types of spectrometers is also possible.

At step 10, chromatography-mass spectrometry data is acquired. This data can be received from various types of mass spectrometers, which can be from a variety of different instrument manufacturers. The acquired data can be in different modes including, e.g., profile and centriod modes.

Each mass spectrometer instrument manufacturer typically has a proprietary data file format for data generated in analyzing a sample. Accordingly, at step 20, the data received from a spectrometer is preferably converted into a common data format, which is independent of each of the instrument manufacturers' proprietary file formats. Converting the data to a common format allows the system software to be easily used with a variety of different instrument file formats. A set of rules can be used for converting the data from a mass spectrometer to a common format. The following is a non-limiting example of one set of possible data conversion rules.

1. The file name is 'filename'. MTD for unsorted data, and 'filename'.MTD.SORT for sorted data.

2. The first line in a file has an ASCII line containing a description of the file type with, e.g., one of the following phrases:

~TEXT

~BINARY

~COMPRESSED BINARY

3. Each run has a run header and each mass spectrum has a spectrum header. The following characters can be used in the first portion of a line and describe the information in that line:

~=Each line is part of the run header and found only at the beginning

>=Each line is part of the spectrum header and found at the beginning of each mass spectrum !=Comments, which can be found in any place in the data file

=End of spectrum marker

4. The data lines have no beginning marker. Each line begins with a mass value (floating point number) followed by a tab, and an intensity value (a floating point number). All lines are CR (carriage return) terminated using, e.g., printf ("\n");

The following is a non-limiting example of data converted to a common data format. By default, data is sorted by scan number, which is indicated below by "RT." RT specifies the point in time of the scan. Scans are acquired periodically, e.g., every second, during each run, which can be, e.g., 90 minutes long. Accordingly, the data is generally a collection of spectra over time. The data is in mass/intensity pairs. For example, the first line of data in spectrum no. 1 (indicated by "SPECNO: 1") is "100.0" and "123". The 100.0 value indicates the mass-to-charge ratio of an ion, and the 123 value indicates its intensity.

```
~TEXT
~Run Header
~Run Header (Cont'd)
>Spectrum Header
>SPECNO: 1
>RT: 0.01
    100.0             123
    101.0              10
    102.0             114
    103.0            1000
    104.1               1
    106.1              15
    107.1              88
    108.1             121
    109.1           15010
    110.1             151
    111.1               1.5
    .
    .
    .
#END OF SPECTRUM
>Spectrum Header
>SPECNO: 2
>RT: 0.07
    100.1              98
    101.2            1111
    102.1               1
    103.0             720
    104.1               5
    105.1             100
    106.1              15
    107.1              88
    108.1             121
    109.1          275010
    110.1           28000
    111.1             300
    .
    .
#END OF SPECTRUM
```

The above data is non mass-sorted. As mentioned, each scan is associated with a time point in the run, and is a collection of data pairs comprising mass-to-charge values and associated intensity values. At step 30, this data is resorted so as to list time-intensity values for each mass-to-charge value within some specified tolerance factor. For each mass, there is a time point and an intensity point.

The following listing is a non-limiting example of the mass sorting of the common format data from the above example data. The sorted data is organized according to mass values (indicated by "MASSNO"). The mass tolerance value is indicated by "MASSTOL". Each line of data includes an RT value, a mass-to-charge value, and an intensity value.

```
~Run Header
~Run Header (Cont'd)
>MASSNO: 100
>MASSTOL: 0.5
    0.01      100.0      123
    0.07      100.1       98
    .
    .
#END MASS 100
>MASSNO: 101
>MASSTOL: 0.5
    0.01      101.0       10
    0.07      101.2     1111
    .
    .
#END MASS 101
>MASSNO: 102
>MASSTOL: 0.5
    0.01      102.1      114
    0.07      102.1        1
    .
    .
#END MASS 102
>MASSNO: 103
>MASSTOL: 0.5
    0.01      103.0     1000
    0.07      103.0      720
    .
    .
#END MASS 103
>MASS NO: 104
>MASSTOL: 0.5
    0.01      104.1        1
    0.07      104.1        5
    .
    .
#END MASS
>MASSNO: 105
MASSTOL: 0.5
    0.07      105.1      100
    .
    .
#END MASS 105
>MASSNO: 106
>MASSTOL: 0.5
    0.01      106.1       15
    0.07      106.1       15
    .
    .
#END MASS 106
>MASSNO: 107
>MASSTOL: 0.5
    0.01      107.1       88
    0.07      107.1       88
    .
    .
#END MASS 107
>MASSNO: 108
>MASSTOL: 0.5
    0.01      108.1      121
    0.07      108.1      121
    .
    .
#END MASS 108
>MASSNO: 109
>MASSTOL: 0.5
    0.01      109.1    15010
    0.07      109.1   275010
    .
    .
#END MASS 109
>MASSNO: 110
>MASSTOL: 0.5
    0.01      110.1      151
    0.07      110.1    28000
    .
    .
#END MASS 110
>MASSNO: 111
>MASSTOL: 0.5
    0.01      111.1        1.5
    0.07      111.1      300
```

-continued

```
    .
    .
    .
#END MASS 111
```

Figure 3:
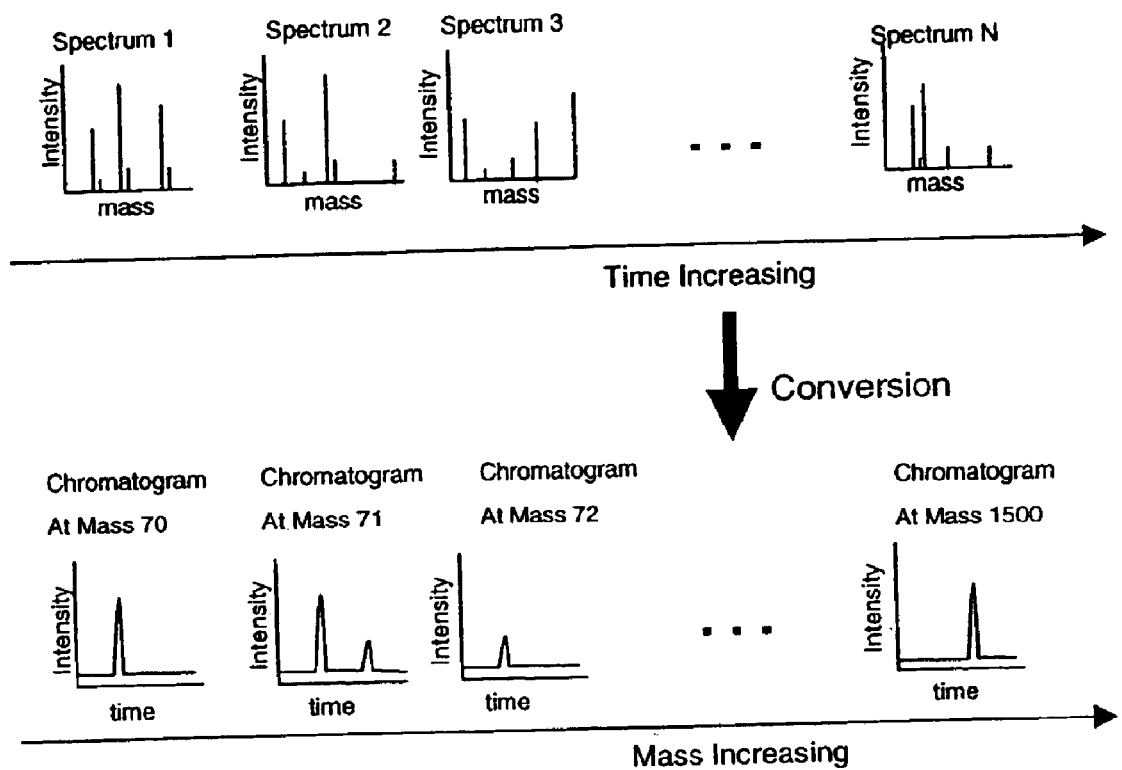
FIG. 3 is an illustration showing the conversion of data from a collection of mass spectra to a collection of mass specific chromatograms.

The conversion of data at step 30 from a collection of mass-intensity data pairs to time-intensity data pairs for given mass ranges is illustrated by way of example in FIG. 3.

At step 40, the signal baseline is determined for each mass-to-charge value. Determining the baseline at each mass-to-charge value allows peak start and end points to be defined and background automatically subtracted. The baseline information is used in the integration step described below.

At step 50, the data can be optionally smoothed if desired prior to integration. Smoothing is helpful in compound detection, particularly when data is choppy The smoothing can be done using a number of known smoothing routines or algorithms including, e.g., Solvitsky-Golay, Gaussian and Boxcar smoothing algorithms.

At step 60, peaks are identified by determining the start data point, the end data point and the top data point of the peak. Overlapping peaks are flagged for further processing during integration as will be described below.

At step 70, the detected peaks are integrated, i.e., the area under each peak is calculated. This area is proportional to the concentration of the compound representing the peak. Integration can be performed using known integration techniques such as, e.g., Boxcar integration. The peaks flagged as overlapping can be further processed by dropping perpendiculars to the baseline or calculating tangents. The criteria for resolving overlapping peak areas can be set by user defined parameters.

At step 80, peaks that have the same start, top and end point values are evaluated to determine if isotope peaks are present. Naturally occurring atomic species are known to have a number of isotopes. If isotope peaks are found, they can optionally be removed from the peak list such that only the most abundant isotopic peak is present on the peak list. Step 80 can be performed prior to Step 70 to reduce integration calculations.

Figure 4:
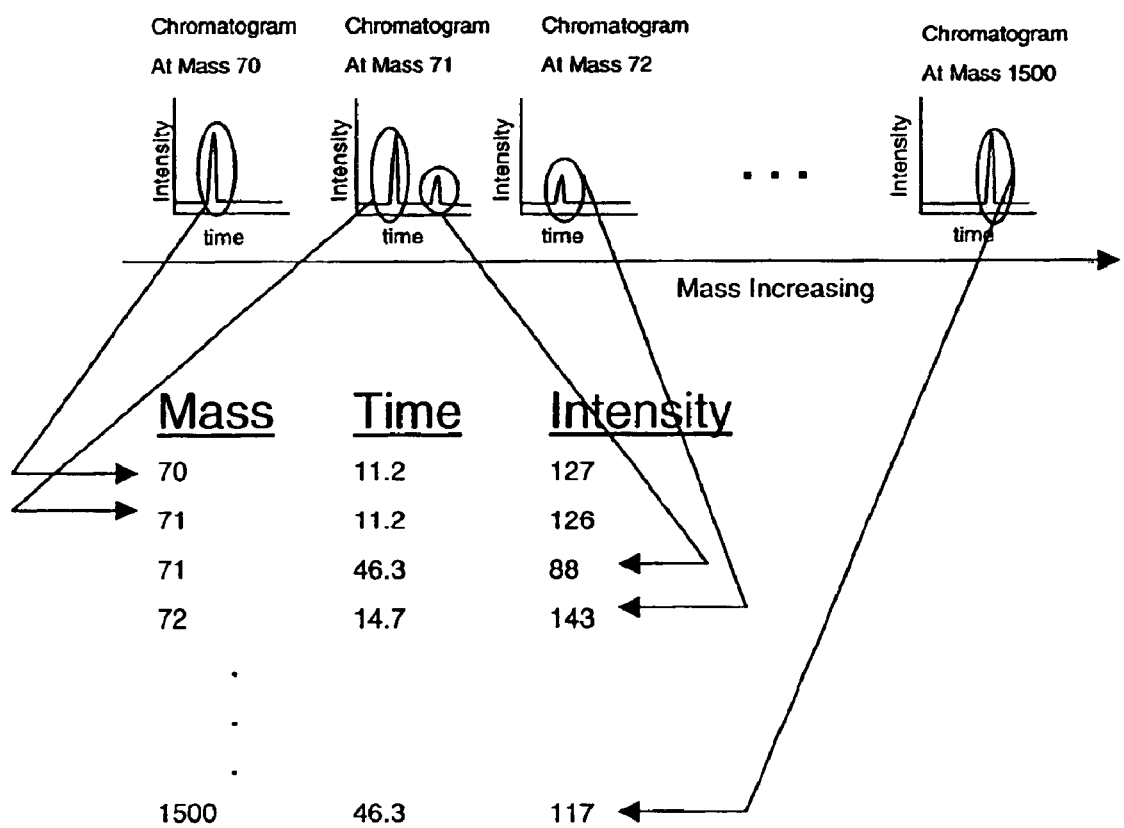
FIG. 4 is an illustration showing the detection of peaks in each mass range and generation of a table of peaks.

At step 90, a table of detected peaks and their respective integrated areas is generated for each type of scan function present in the run as shown by way of example in FIG. 4.

At step 100, a separate table or list of peaks is generated containing those peaks that have been found to co-elute or overlap. The user can define what parameters to use for defining co-eluting peaks. For example, the user can require co-eluting peaks to have identical start, top and end values. The co-eluting or overlapping peaks are compared at step 110 to determine if they occur from the same compound as possible adducts or fragments. The integrated areas from multiple peaks that have been labeled as coming from the same compound can be combined or weighted and combined under user direction at step 120.

At step 130, the resulting peak lists are loaded into results databases for use in further analysis. The peak lists preferably include for each peak the start, end and top data points as well as the relative retention times and the corrected integrated areas.

From the peak lists in the database, compound profiles such as metabolite profiles can be generated. Also, tentative compound identities can be assigned.

The above described process is particularly suitable for analyzing mass spectroscopic data obtained from chromatographically fractioned mixtures. It should be noted, however, that the process can also be used for identifying peaks in complex mixtures that are not chromatographically separated.

The process described above can also be used for analyzing virtually any spectroscopic data obtained from any of a wide variety of spectroscopic approaches. Representative examples of suitable spectroscopic approaches include, but are not limited to, mass spectrometry, ultraviolet spectroscopy, infrared spectroscopy, atomic spectroscopy, NMR spectroscopy, Raman spectroscopy, emission spectroscopy, and the like. In the non limiting example process described above, a mass spectrometer is used with mass values being the spectral parameter in the resulting data. The process can be used with other spectrometers by substituting mass values with the particular spectral parameter values associated with the spectrometer used. For example, the spectral parameter for infrared spectrometers and UV-visible spectrometers is wavelength. The spectral parameter for atomic spectrometers is emission wavelength or atomic mass. The spectral parameter for NMR spectrometers is chemical shift from reference.

The spectral parameter can be an indexed or window value. In the examples described above, a specific mass values are used. However, in accordance with some embodiments, the values can be a window or range, which speeds calculations due to fewer data points. A window is appropriate particularly when the background and the compound(s) of interest and their spectral and separation behaviors are better known and understood. For example, analysis for specific drug components in a well understood albeit complex mixture (e.g., urine) might be suitable to use of window values.

A wide variety of compounds can be analyzed in accordance with the processes described herein. Such compounds can include, but are not limited to, proteins, peptides, olignucleotides, polynucleotides, organic species, such as drugs, toxic agents, etc.

The peak detection process is preferably implemented in software, and accordingly one of the useful implementations of the invention is as a set of instructions (program code) in a code module resident in the random access memory of a computer. Until required by the computer, the set of instructions may be stored in another computer memory, e.g., in a hard disk drive, or in a removable memory such as an optical disk (for eventual use in, e.g., a CD ROM) or floppy disk (for eventual use in a floppy disk drive), or downloaded via the Internet or some other computer network. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the specified method steps.

Having described various embodiments of the present invention, it should be apparent that modifications can be made without departing from the spirit and scope of the invention.

What is claimed is:

1. A method for identifying peaks in spectral data of compounds, the spectral data having spectral parameters values the method comprising:
converting the spectral data to converted data comprising a time-intensity data pair for each spectral parameter value;
detecting peaks in the converted data;
integrating peak areas;
identifying any coeluting peaks, and combining any coeluting peak areas determined to be associated with the same compound; and
generating a list of detected peaks and their corresponding peak areas, including any combined coeluting peak areas.

2. The method of claim 1, further comprising smoothing the converted data prior to integration.

3. The method of claim 2, wherein said smoothing is performed using Solvitsky-Golay, Gaussian or Boxcar smoothing algorithms.

4. The method of claim 1, further comprising specifying parameters for defining coeluting peaks.

5. The method of claim 4, wherein coeluting peaks are defined by generally identical start, top and end peak positions.

6. The method of claim 1, wherein said method is performed using a computer.

7. The method of claim 1, further comprising converting the spectral data to an instrument independent common format.

8. The method of claim 1, further comprising identifying and removing any isotopic peaks from detected peaks.

9. The method of claim 1, wherein said spectral data comprises chromatography-mass spectrometry data.

10. The method of claim 1, wherein said spectral data is acquired using mass spectrometry and wherein said spectral parameter values comprise mass values.

11. The method of claim 1, wherein said spectral data is acquired using infrared spectroscopy, and wherein said spectral parameter values comprise wavelength values.

12. The method of claim 1, wherein said spectral data is acquired using UV-visible spectroscopy, and wherein said spectral parameter values comprise wavelength values.

13. The method of claim 1, wherein said spectral data is acquired using atomic spectroscopy, and wherein said spectral parameter values comprise emission wavelength or atomic mass values.

14. The method of claim 1, wherein said spectral data is acquired using NMR spectroscopy, and wherein said spectral parameter values comprise chemical shift from reference values.

15. The method of claim 1, wherein detecting peaks in the converted data comprises identifying start, top, and end values for each peak.

16. The method of claim 1, wherein detecting peaks in the data includes determining a baseline for each spectral parameter value.

17. The method of claim 1, wherein each spectral parameter value is a specific value, or a range of values.

18. A computer program product in computer-readable for identifying peaks in spectral data of compounds, the spectral data having spectral parameters values, the computer program product comprising instructions enabling a computer to:
convert the spectral data to converted data comprising a time-intensity data pair for each spectral parameter value;
detect peaks in the converted data;
Integrate peak areas;
identify any coeluting peaks, and combine coeluting peak areas determined to be associated with the same compound; and
generate a list of detected peaks and their corresponding peak areas, including any combined coeluting peak areas.

19. The computer program product of claim 18, further comprising instructions enabling a computer to smooth the converted data prior to integration.

20. The computer program product of claim 19, wherein smoothing is performed using Solvitsky-Golay, Gaussian or Boxcar smoothing algorithms.

21. The computer program product of claim 18, further comprising instructions enabling a computer to convert the spectral data to an instrument independent common format.

22. The computer program product of claim 18, further comprising instructions enabling a computer to identify and remove any isotopic peaks from detected peaks.

23. The computer program product of claim 18, wherein said spectral data is acquired using mass spectrometry, and wherein said spectral parameter values comprise mass values.

24. The computer program product of claim 18, wherein said spectral data is acquired using infrared spectroscopy, and wherein said spectral parameter values comprise wavelength values.

25. The computer program product of claim 18, wherein said spectral data is acquired using UV-visible spectroscopy, and wherein said spectral parameter values comprise wavelength values.

26. The computer program product of claim 18, wherein said spectral data is acquired using atomic spectroscopy, and wherein said spectral parameter values comprise emission wavelength or atomic mass values.

27. The computer program product of claim 18, wherein said spectral data is acquired using NMR spectroscopy, and wherein said spectral parameter values comprise chemical shift from reference values.

28. The computer program product of claim 18, wherein the peaks are detected in the converted data by identifying start, top, and end values for each peak.

29. The computer program product of claim 18, wherein peaks in the data are detected by determining a baseline for each spectral parameter value.

30. The computer program product of claim 18, wherein each spectral parameter value is a specific value or a range of values.

31. A system for generating in spectral data of compounds, the spectral data having spectral parameters values and for identifying peaks therein, said system comprising:
a spectrometer for generating the spectral data from a sample; and
a computer system for analyzing the spectral data, said computer system comprising at least one processor, memory associated with the at least one processor, a display and a program supported in the memory for identifying peaks in spectral data, the program comprising instructions enabling the computer system to:

convert the spectral data to converted data comprising a time-intensity data pair for each spectral parameter value;

detect peaks in the converted data;

integrate peak areas;

identify any coeluting peaks, and combine coeluting peak areas determined to be associated with the same compound; and generate a list of detected peaks and their corresponding peak areas, including any combined coeluting peak areas.

32. The system of claim 31, wherein said program further includes instructions enabling the computer system to smooth the converted data prior to integration.

33. The system of claim 32, wherein smoothing is performed using Solvitsky-Golay, Gaussian or Boxcar smoothing algorithms.

34. The system of claim 31, wherein said program further includes instructions enabling a computer to convert the spectral data to an instrument independent common format.

35. The system of claim 31, wherein said program further includes instructions enabling the computer system to identify and remove any isotopic peaks from the detected peaks.

36. The system of claim 31, wherein said computer system comprises a personal computer.

37. The system of claim 31, wherein said computer system comprises a workstation linked to said spectrometer and a server computer.

38. The system of claim 31, wherein said spectrometer comprises a mass spectrometer, and wherein said spectral parameter values comprise mass values.

39. The system of claim 31, wherein said spectrometer comprises an infrared spectrometer, and wherein said spectral parameter values comprise wavelength values.

40. The system of claim 31, wherein said spectrometer comprises a UV-visible spectrometer, and wherein said spectral parameter values comprise wavelength values.

41. The system of claim 31, wherein said spectrometer comprises an atomic spectrometer, and wherein said spectral parameter values comprise emission wavelength or atomic mass values.

42. The system of claim 31, wherein said spectrometer comprises an NMR spectrometer, and wherein said spectral parameter values comprise chemical shift from reference values.

43. The system of claim 31, wherein the peaks are detected in the converted data by identifying start, top, and end values for each peak.

44. The system of claim 31, wherein peaks in the data are detected by determining a baseline for each spectral parameter value.

45. The system of claim 31, wherein each spectral parameter value is a specific value or a range of values.

* * * * *